United States Patent [19]

Turner, Sr.

[11] Plant 4,919

[45] Nov. 2, 1982

[54] VARIEGATED PITTOSPORUM PLANT

[76] Inventor: Ted L. Turner, Sr., 6503 S. Padre Island Dr., Corpus Christi, Tex. 78412

[21] Appl. No.: 263,095

[22] Filed: May 12, 1981

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Stewart N. Rice

[57] ABSTRACT

A pittosporum plant which has a dwarf habit of growth, the leaf blades being variegated and generally being medium green in color with pale yellow margins, the width of the pale yellow variegation being irregular.

1 Drawing Figure

DESCRIPTION OF THE INVENTION

The present invention relates to a new and distinct variety of pittosporum plant of the variety *Pittosporum tobira,* which originated and was discovered by me as a cultivated sport of the variety known as "Wheeler's dwarf". The sport was discovered by me on a *Pittosporum tobira* "Wheeler's dwarf" being grown and cultivated by me in a nursery in Corpus Christi, Tex. Upon discovery of the sport, I observed that the leaves of the sport, unlike the dark green leaves of the parent plant, were variegated and were medium green in color with pale yellow margins. In order to determine whether or not the sport would asexually reproduce, I performed an initial experiment wherein I made five cuttings from the sport, and from such five cuttings I was able to asexually reproduce four plants on their own roots, all of which plants had the same characteristics as the sport, and all four of which constituted a new and distinct variety of pittosporum. In the initial experiment, the fifth cutting did not survive.

Subsequent to the initial experiment, in due course I asexually reproduced numerous of the new and distinct variety of pittosporum from other cuttings of the original sport, as well as from cuttings from the four first generation plants grown in the initial experiment described above, and all of the descendant plants show the same characteristics as the original sport. As a result of extensive observations and tests which are not described in full herein for sake of brevity, it is my opinion and I am convinced that my new plant is a new variety of pittosporum which is distinguished from all other varieties of which I am aware as evidenced by the following unique combination of principlal characteristics which are outstanding therein:

(1) A dwarf and compact habit of growth makes it especially suitable as a border plant, as a small hedge, in planter boxes and as a pot plant;

(2) A slow rate of growth which is advantageous in that frequent pruning is not necessary to maintain the shrub in a pleasing shape;

(3) An ability to be asexually reproduced;

(4) The ability to provide a shrub having a plurality of colors by reason of the variegated nature of the broadleaf evergreen leaves of the new variety, which leaves are medium green with pronounced variegated margins of irregular depth of pale yellow color, and which leaves grow alternately in a whorl on the branches;

(5) The ability to tolerate pruning in order that attractive shapes can be maintained.

Asexual reproductions of my new variety as by cuttings shows that the foregoing characteristics and distinction come true to form and are established and transmitted through succeeding propagations.

The accompanying drawing shows a typical young specimen plant of my new variety and the variegated nature and color of the leaves thereof. Even though the plant illustrated is young, the leaves are mature leaves and the colors shown are the colors for the mature leaves and are not the colors for new leaves hereafter described. The true color of the foliage is described in the following description and is best depicted by the views in the drawings which depict the color as nearly as true as is reasonably possible in a color illustration of this type.

The following is a detailed description of my new variety of pittosporum, with color numbers in accordance with the Pantone Matching System of colors for printing inks, 16th edition, published by Pantone, Inc., 1977. Terms used to describe colors are those of ordinary significance.

THE PLANT

Parentage: A cultivated sport of "Wheeler's dwarf" variety of *Pittosporum tobira.*

Growth habit: Compact, dwarf, slow growing; the height of an unpruned mature plant will probably be from about 1.5 to 2 meters, but has not yet been determined. The plant grows full from just above ground level upward, with the width of the plant about the same as the height.

Hardiness: Adapted to seaside planting; tolerates droughts; will not withstand prolonged and severe freezing weather; most suitable for the Southern United States from California to Florida, in the areas known as Zones 9 and 10.

Branches: The plant is tightly branched from just above ground level with main branches ascending and with branching at each node. The plant does not develop a central leader or trunk. New growth of branches is light green changing to light brown and later to dark brown as branches mature.

Foliage:

*Type.*—Broadleaf evergreen; petioled; grow alternately in a whorl on branches.

*Shape.*—Oblanceolate, more or less, with entire margins. Apex is obtuse, and base is acuminate.

*Petioles.*—Length — from about 3 to 5 mm; color light green.

*Leaf Size.*—Length of mature leaf from about 4 to 8 cm; width of mature leaf about 13 to 25 mm. Size of leaf varies according to sunshine conditions at the time the leaf is produced, with larger leaves being produced under cloudy conditions than under sunny conditions.

*Venation.*—Pinnately. Midrib on under surface prominent and readily apparent; on upper surface midrib is clearly visible and pronounced, and is of a lighter color than surrounding areas of the leaf; lateral veins are not readily apparent.

*Leaf color.*—Mature leaves: upper surface — medium green, Color No. 392U, with variegated margins of pale yellow, Color No. 113U; the line of intersection between the green of the central area and the yellow of the margin being relatively sharp, but being an irregular line such that the depth of the margin is irregular, the width of the margin varying from about 1 to 10 mm; under surface — similar to the upper surface but lighter colors. New leaves: upper surface — dark green, Color No. 378U with marginal variegations light green, Color No. 390U; nature and width of margins same as on mature leaves. Most of the variegation is on the outer half of the leaf blade.

*Leaf texture.*—Tough, leathery; smooth; upper surface — semi-glossy; lower surface — dull.

*Flowers.*—The nature of the flowers that will be produced has not been determined. Flowers of the parent and of related plants are an ivory color, each flower being about 15 mm in diameter; and, it is expected that the flowers on the plant herein claimed and described will be similar to those on the parent.

To further describe my new variety of pittosporum, it is very similar in size and growth habit to the "Wheeler's dwarf" variety of *Pittosporum tobira* except for the variegated nature of the leaf blades on my new variety, and except that my new variety is slower growing than the "Wheeler's dwarf". The green portion of the leaves on my new variety are generally a lighter green than the green of the "Wheeler's dwarf". There is a variegated form of *Pittosporum tobira* known as *Pittosporum tobira variegata.* My new variety differs from *Pittosporum tobira variegata* in that it is slower growing and in that my new variety has a dwarf habit of growth. Also the leaves on the *Pittosporum tobira variegata* are of a different color than on my new variety, the leaf blades of the *Pittosporum tobira variegata* having a creamy white margin as opposed to the pale yellow margin of my new variety.

I claim:

1. A new and distinct variety of pittosporum, substantially as herein shown and described, characterized particularly as to novelty by the unique combination of: A dwarf and compact habit of growth makes it especially suitable as a border plant, as a small hedge, in planter boxes and as a pot plant; a slow rate of growth which is advantageous in that frequent pruning is not necessary to maintain the shrub in a pleasing shape; an ability to be asexually reproduced; the ability to provide a shrub having a plurality of colors by reason of the variegated nature of the leaves of the new variety, which leaves are medium green with pronounced variegated margins of irregular depth of pale yellow color, and which leaves grow alternately in a whorl on the branches; and the ability to tolerate pruning in order that attractive shapes can be maintained.

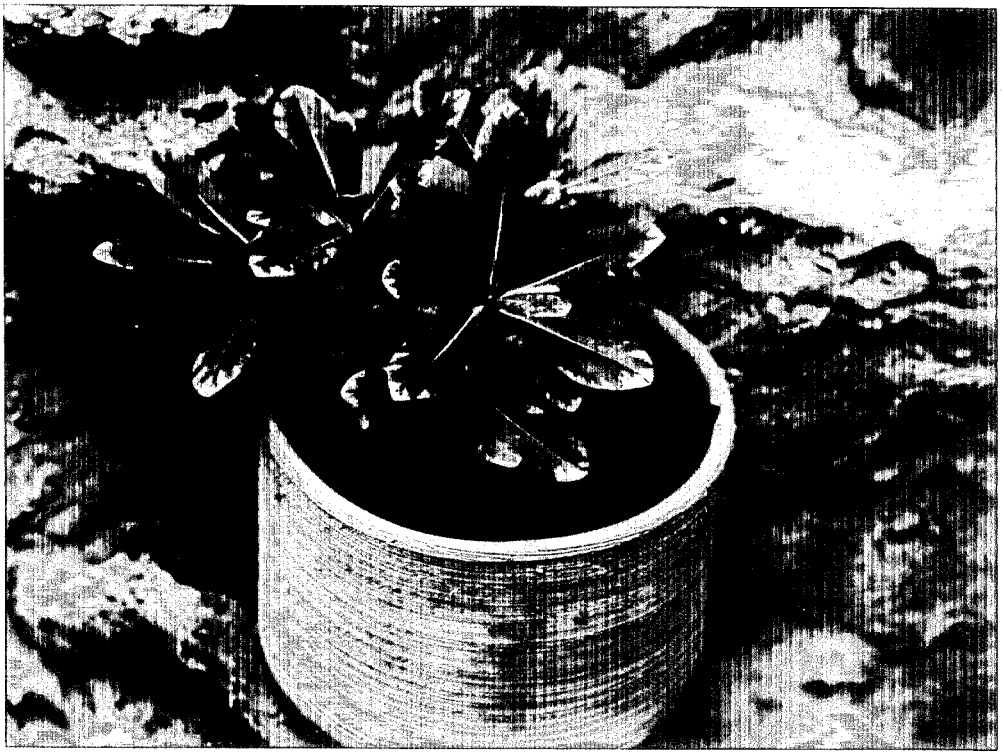

* * * * *